United States Patent
Bystricky

(10) Patent No.: US 8,290,576 B2
(45) Date of Patent: Oct. 16, 2012

(54) MODELING THE ELECTRICAL ACTIVITY OF THE HEART BY A SINGLE DIPOLE, CONCURRENTLY ESTIMATING SUBJECT AND MEASUREMENT RELATED CONDITIONS

(76) Inventor: Werner Bystricky, Langenburg (DE)

( * ) Notice: Subject to any disclaimer, the term of this patent is extended or adjusted under 35 U.S.C. 154(b) by 251 days.

(21) Appl. No.: 12/742,436

(22) PCT Filed: Nov. 10, 2008

(86) PCT No.: PCT/EP2008/009472
§ 371 (c)(1),
(2), (4) Date: May 20, 2010

(87) PCT Pub. No.: WO2009/062651
PCT Pub. Date: May 22, 2009

(65) Prior Publication Data
US 2011/0105924 A1    May 5, 2011

(30) Foreign Application Priority Data
Nov. 12, 2007  (EP) ..................................... 07021918

(51) Int. Cl.
*A61B 5/04*    (2006.01)
(52) U.S. Cl. ....................................................... 600/512
(58) Field of Classification Search ........... 600/508–528
See application file for complete search history.

(56) References Cited

U.S. PATENT DOCUMENTS

| | | | |
|---|---|---|---|
| 4,949,725 A | 8/1990 | Raviv | |
| 5,711,304 A | 1/1998 | Dower | |
| 5,803,084 A | 9/1998 | Olson | |
| 6,856,830 B2 | 2/2005 | He | |
| 7,016,719 B2 | 3/2006 | Rudy | |
| 2006/0047212 A1 | 3/2006 | Wei | |

FOREIGN PATENT DOCUMENTS

WO    2005072607 A    8/2005

OTHER PUBLICATIONS

Malmivuo and Plonsey, Bioelectromagnetism—Principles and Applications of Bioelectric and Biomagnetic Fields; Oxford University Press, 1995—in part, including sections 8.2.2, 11.4, 11.6, 15 mentioned in application.
Press et al., Numerical Recipes: The Art of Scientific Computing; Cambridge University Press, 2007—in part, including section 10.6.
Edenbrandt and Pahlm, "Vectorcardiogram Synthesized From a 12-lead ECG: Superiority of the Inverse Dower Matrix" J. Electrocardiology 21(4):361-367 (1988).
Frank, "An Accurate, Clinically Practical System for Spatial Vectorcardiography" Circulation 13:737-749 (1956).
Savard et al., "Representation of cardiac electrical activity by a moving dipole for normal and ectopic beats in the intact dog" Circulation Research 46:415-425 (1980).

(Continued)

*Primary Examiner* — Niketa Patel
*Assistant Examiner* — Hiba El-Kaissi

(57) ABSTRACT

A method is provided which relates to the identification of the electrical activity in the heart in terms of a single dipole, which may be considered moving or non-moving, based on measurements from a body surface electrocardiogram (ECG), concurrently estimating subject and measurement related conditions. The invention further relates to computer program for performing said method, a data carrier containing said program as well a computer device for performing said program. A device for performing said method is also disclosed.

16 Claims, 8 Drawing Sheets

OTHER PUBLICATIONS

International Search Report issued in PCT Application No. PCT/EP2008/009472 (international counterpart to U.S. Appl. No. 12/742,436).

Written Opinion issued in PCT Application No. PCT/EP2008/009472 (international counterpart to U.S. Appl. No. 12/742,436).

International Preliminary Report on Patentability issued in PCT Application No. PCT/EP2008/009472 (international counterpart to U.S. Appl. No. 12/742,436).

Fukuoka et al., "Applicability of the Single Equivalent Moving Dipole Model in an Infinite Homogeneous Medium to Identify Cardiac Electrical Sources: A Computer Simulation Study in a Realistic Anatomic Geometry Torso Model" IEEE Tranactions on Biomedical Engineering, IEEE Service Center, Piscataway NJ US 53(12):2436-2444 (Dec. 2006).

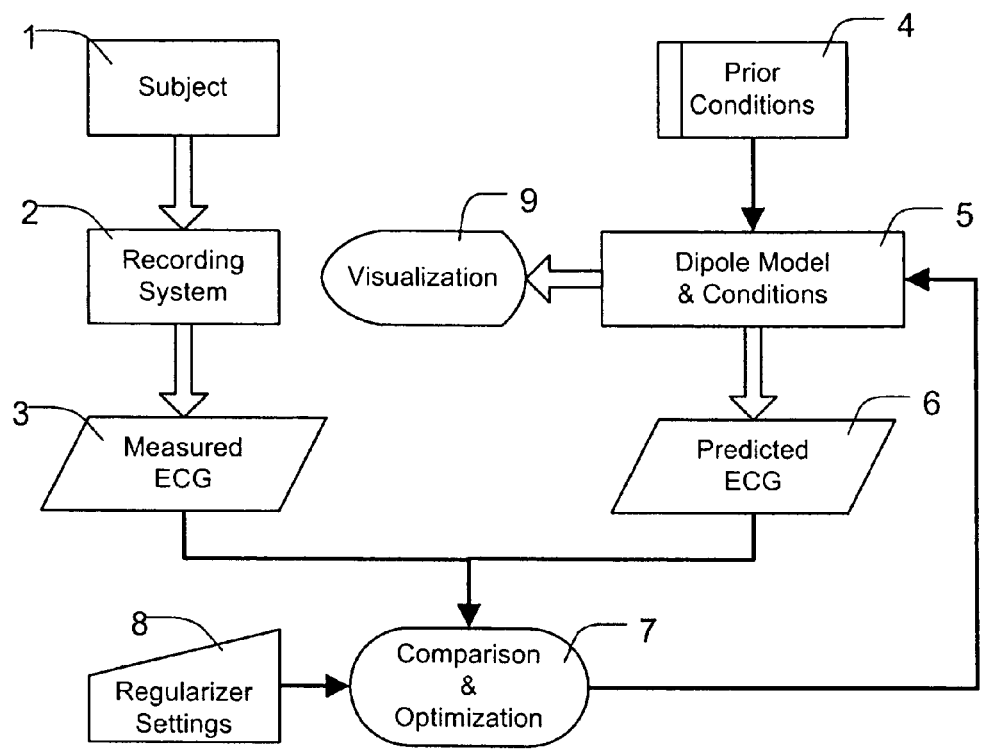
Figure 1: Flow diagram

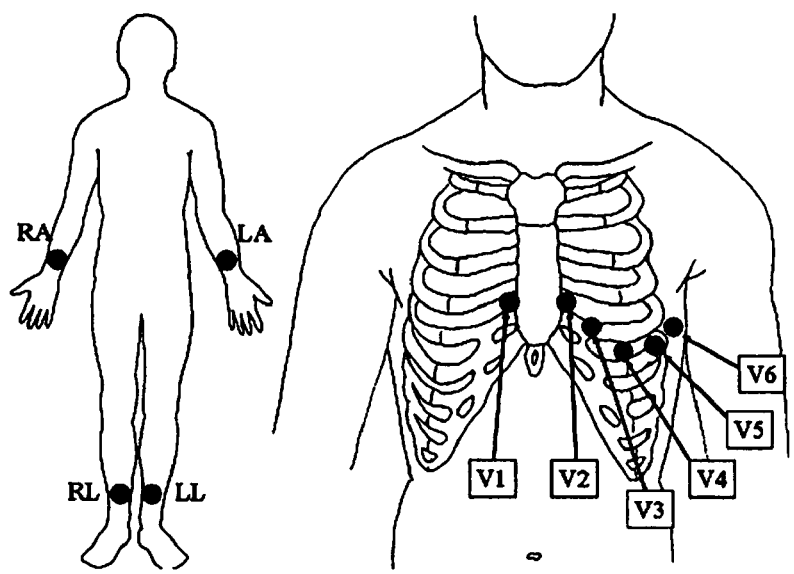
Figure 2: Electrode positions for the standard 12-lead ECG
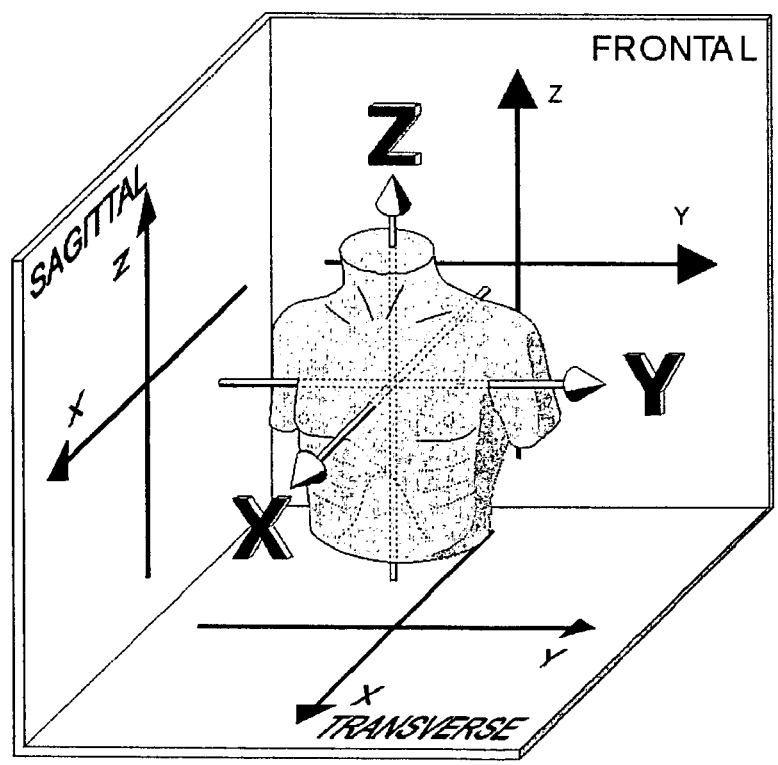
Figure 3: Coordinate system

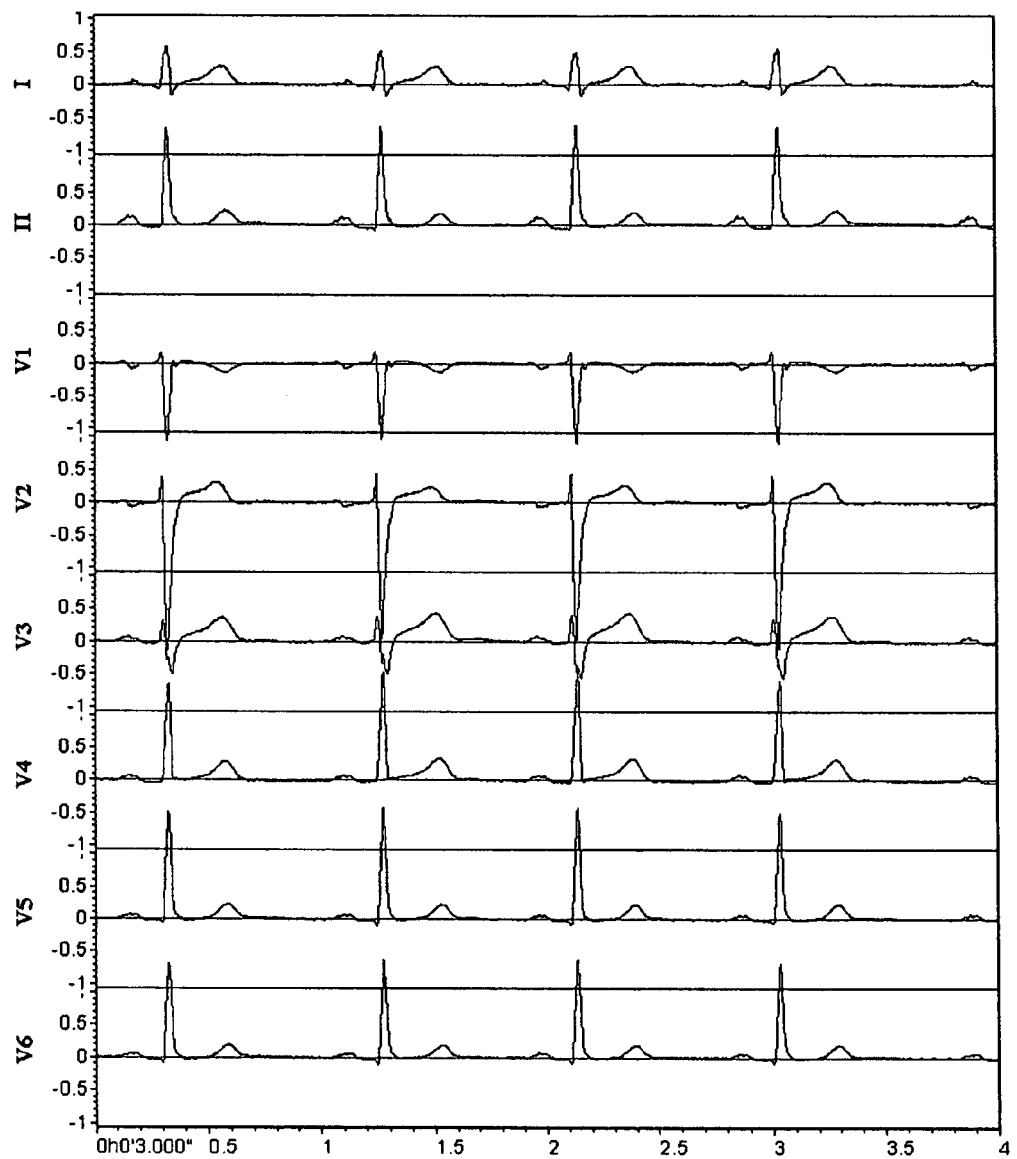
Figure 4: ECG of example 1

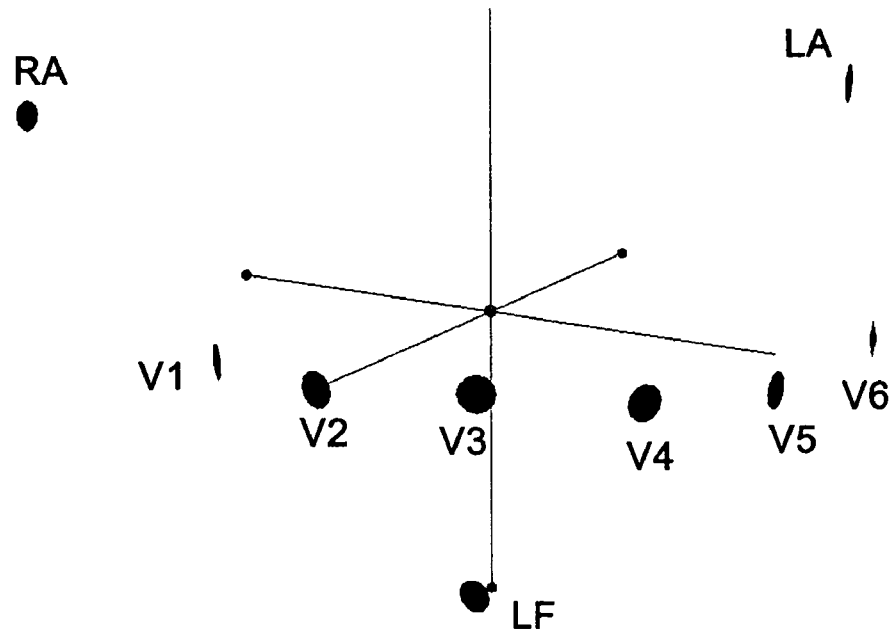
(a) Prior electrode positions
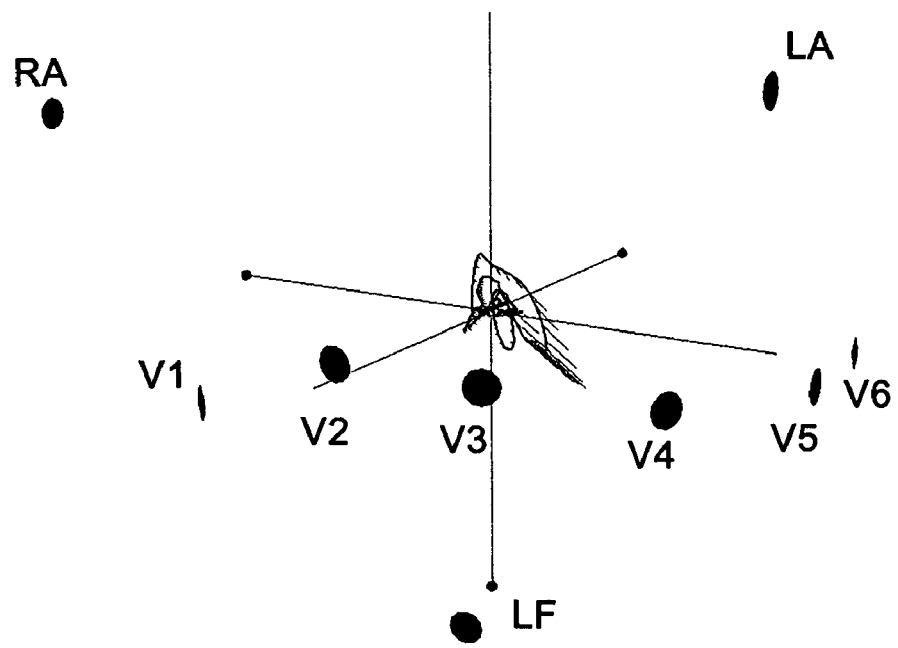
(b) Adapted electrode positions
Figure 5: Model adaptation, example 1

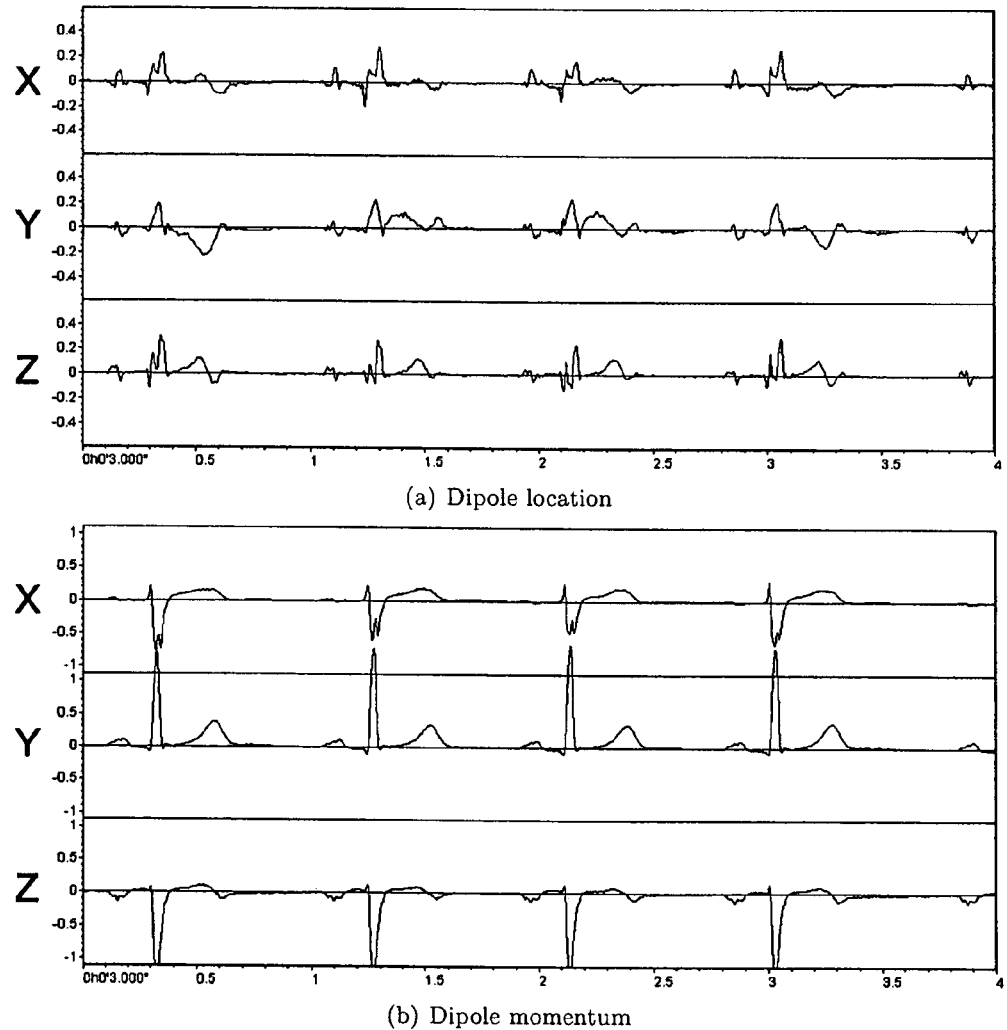
Figure 6: Estimated spatial time courses of the moving dipole of example 1

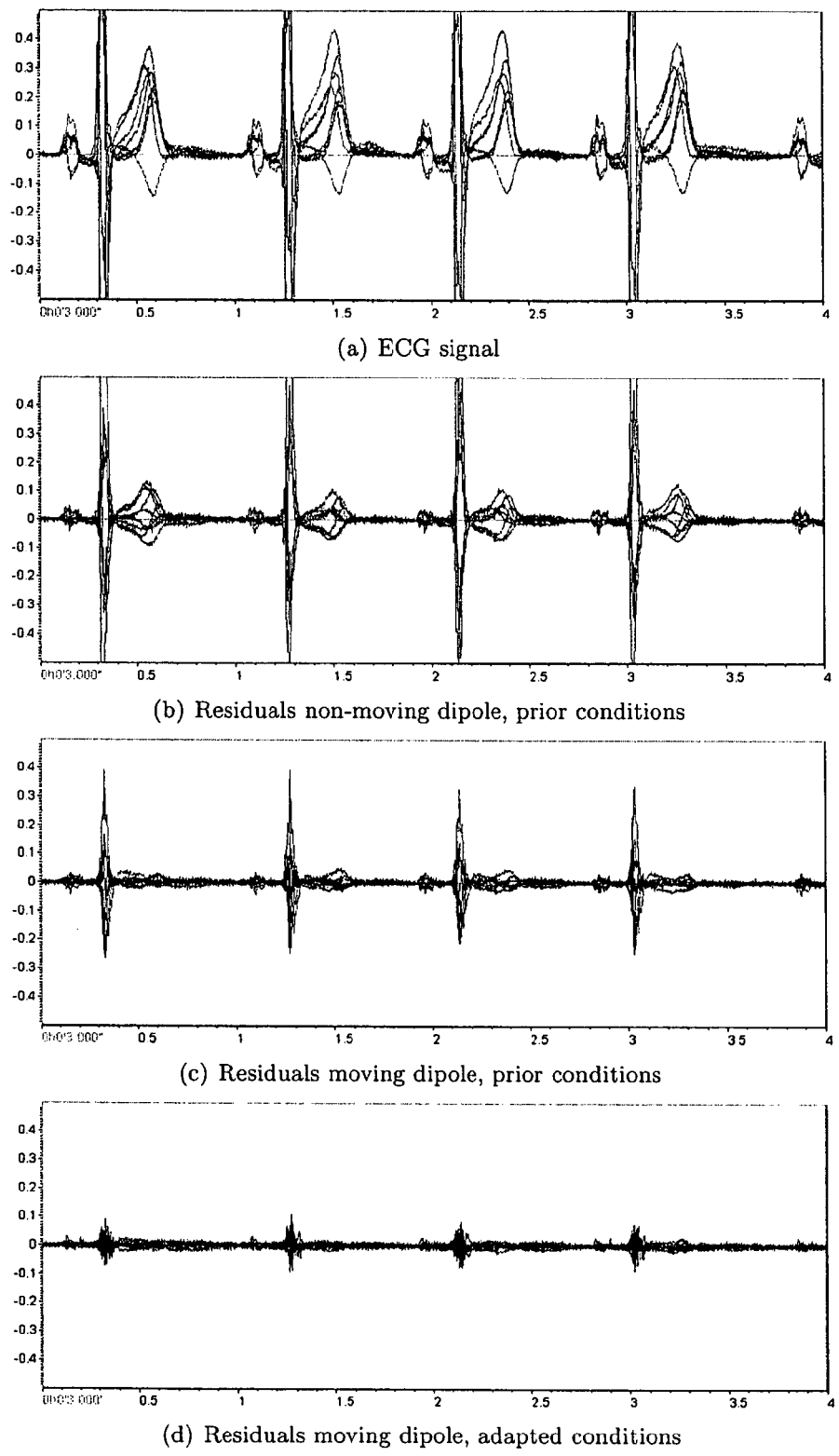
Figure 7: Residual comparison

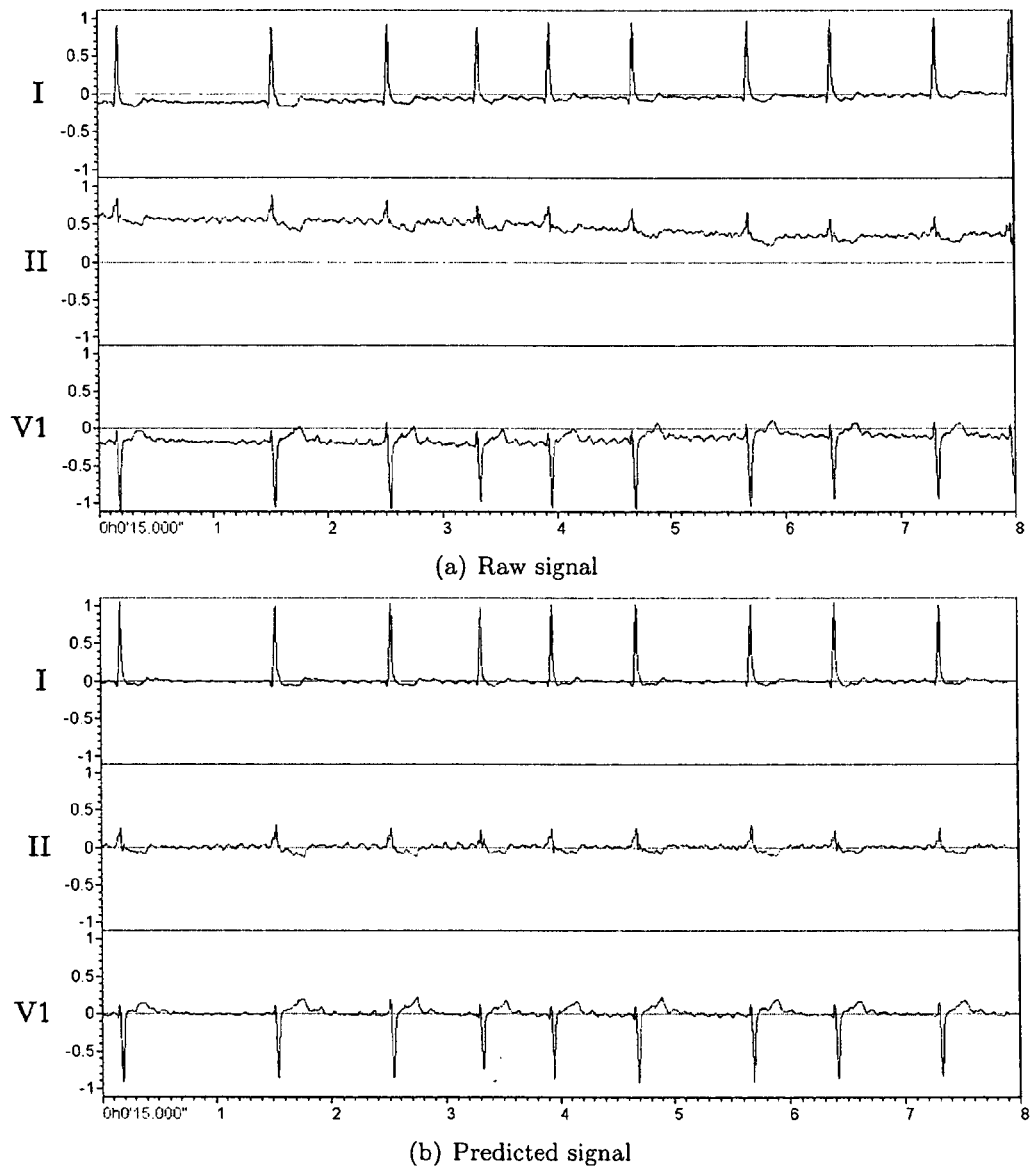
Figure 8: ECG with atrial fibrillation, example 2

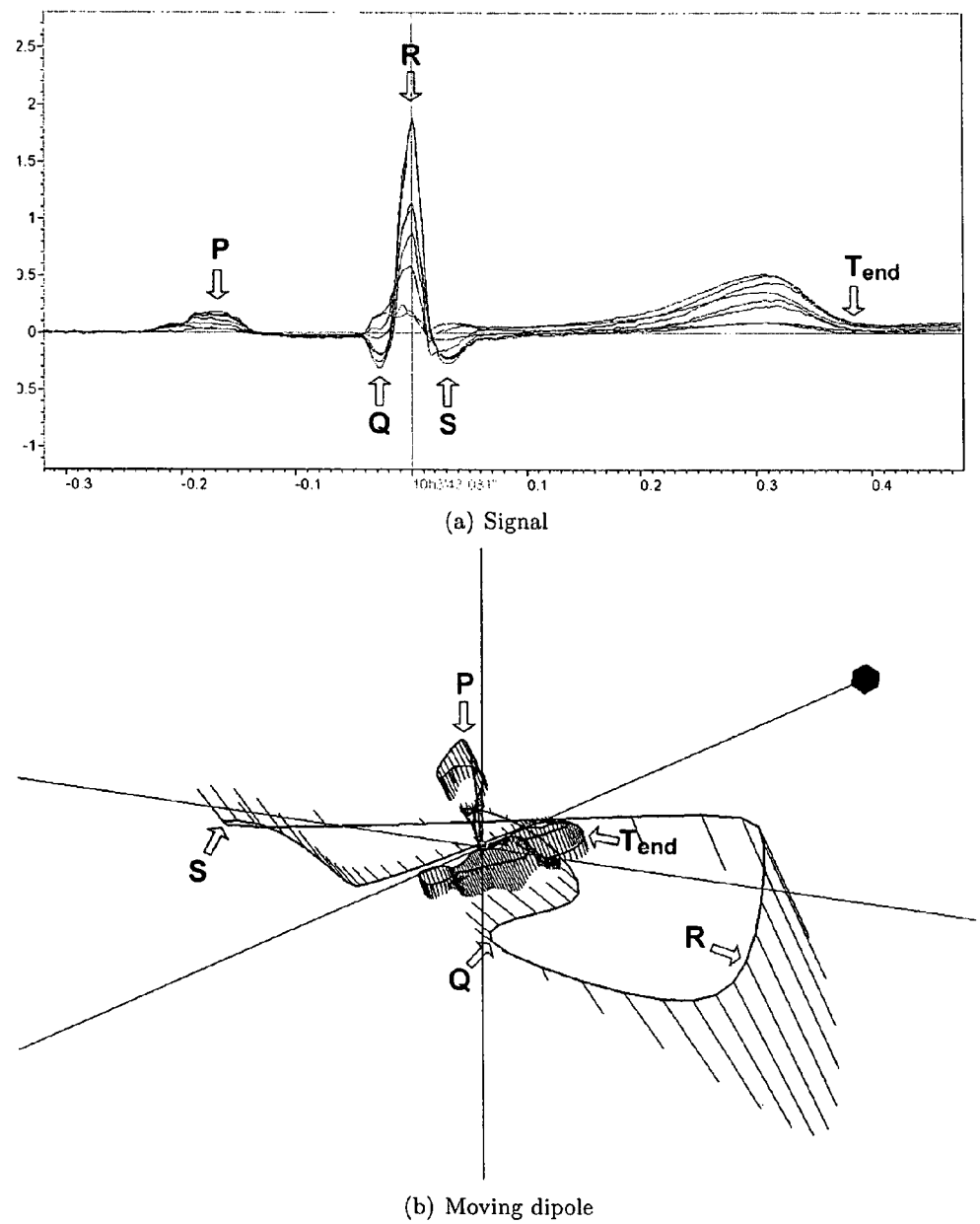
(a) Signal
(b) Moving dipole
Figure 9: Heartbeat

US 8,290,576 B2

MODELING THE ELECTRICAL ACTIVITY OF THE HEART BY A SINGLE DIPOLE, CONCURRENTLY ESTIMATING SUBJECT AND MEASUREMENT RELATED CONDITIONS

CROSS-REFERENCE TO RELATED APPLICATIONS

This application is a national phase entry under 35 U.S.C. §371 of International Patent Application PCT/EP2008/009472, filed Nov. 10, 2008, published as International Patent Publication WO 2009/062651 on May 22, 2009, which claims priority to European Patent Application No. 07 021 918.3 now granted as European Patent No. 2 057 942.

TECHNICAL FIELD

The method relates to the identification of the electrical activity in the heart in terms of a single dipole, which may be considered moving or non-moving, based on measurements from a body surface electrocardiogram (ECG). This method further relates to the influence of body shape, tissue conductivity and inhomogeneity as well as real electrode positions onto an ECG measurement, thus improving comparison of ECG characteristics from different subjects or ECG recordings.

BACKGROUND ART

The electrical activity of the heart is typically measured at the body surface by a set of electrodes. Two or more electrodes are combined to form a lead (e.g. limb leads are measuring the potential difference at two electrodes, precordial leads are measuring the potential difference of one precordial electrode to the central terminal, which is calculated as mean value of the potential measured at the limb electrodes). A lead measurement may be interpreted as a projection of the hearts equivalent dipole onto the lead vector where the origin of that dipole is located somewhere in the center of the heart.

The widely used standard 12-lead ECG thus provides 12 different views onto the hearts electrical activity, where the view directions (i.e. the lead vectors) are considered as known. The precordial leads e.g. correspond to vectors pointing from the center of the heart to the electrode position and the limb leads correspond to the edges of the well-known Einthoven's triangle ([5], section 15). These lead vectors however are only rough estimates and they do not account for subject specific conditions like body geometry or tissue conductivity. Furthermore the standard 12-lead ECG does not reveal direct information about the origin of the electrical activity within the heart. Typically, localization information is derived indirectly by interpretation of ECG forces, i.e. dipole momentum characteristics.

Many different lead sets have been proposed. Vectorcardiography (VCG) e.g. intends to arrange electrodes in a way, that the resulting lead vectors are approximately orthonormal ([3], [6]). However these lead configurations have been determined with help of a torso model, which also does not care for subject specific body conditions.

Attempts have been made to map standard 12-lead ECG measurements onto the VCG lead set, using a fixed linear transformation matrix [1], [2]. This approach is equivalent to modeling a non-moving dipole using standard 12-lead measurements where all body and measurement related conditions are considered fixed and given.

Attempts have been made to apply a single moving dipole model onto the electrical activity of the heart [9]. However those methods rely on given data or assumptions about the true heart position, body shape, tissue inhomogeneity and the real electrode positions.

Electrocardiographic imaging methods try to determine the potential distribution at the heart by solving the so-called inverse problem of electrocardiography ([4], [8]). They may use larger sets of dipoles to describe the electrical activity of the heart. However those individual dipole locations are fixed within the heart and the whole body geometry has to be obtained by other (expensive) measuring devices (e.g. CT scan, MRI or X-ray). Furthermore those approaches typically require a larger number of electrodes compared to the standard 12-lead ECG.

ECG measurements taken at the body surface are influenced by the location of the source of the electrical activity within the heart, by body geometry, tissue conductivity, real electrode positions and other non-cardiac electrical sources (e.g. muscle activity, electrical fields created by electrical devices). This hinders the comparison of ECG measurements and makes it difficult to determine global parameters for the identification of heart diseases (e.g. ST elevation or depression, assessment of T-wave properties).

It follows that there is a need for a method which allows to determine the electrical activity of a heart of a subject with improved precision, using standard ECG measurement devices, taking into account subject and measurement related conditions without requiring extensive measurements of the body characteristics of the subject in question.

To solve this problem a method is herein disclosed that describes the electrical activity of the heart in terms of a 3-dimensional process using measurements from body surface potentials and some weak prior knowledge about subject and measurement related conditions, where those subject and measurement related conditions are adjusted on basis of the data acquired during the body surface potential measurements.

SUMMARY OF THE INVENTION

This invention relates to a method for identifying the electrical activity in the heart of an animal body in terms of a single dipole, which may be considered moving or non-moving, from measurements from body surface potentials, concurrently estimating subject and measurement related conditions. This method comprises the steps of: measuring the body surface potential of an animal body by multiple leads, said potential measured over a length of time for a number of time points, thereby producing measurements of lead voltages at the given number of time points; providing prior values for a time course of the dipole location, the electrode positions on the body, the baseline at each lead, as well as conductivity parameters, characterizing the electrical conductivity and tissue inhomogeneity of the subject, herein after referred to as prior conditions; providing initial values for the time course of the 3-dimensional momentum vector together with initial values for all conditions mentioned above; providing regularizer settings for the variable parameters and time courses of variable parameters. In a next step the lead voltage for each lead and each time point is predicted by calculating the scalar product of the dipole momentum vector with the appropriate lead vector, wherein the lead vectors are determined by the dipole location, the positions of all referenced electrodes and the conductivity parameters. In the next step the error function as the sum of a measure of the deviation of the measured lead voltages to the predicted lead voltages and the regularizer function values of said regularizer settings is calculated. This error function is minimized by applying an optimization algorithm, varying the dipole momentum and optionally any of the conditions mentioned above. Finally the time courses of the dipole momentum and all conditions mentioned above are obtained. The invention also relates to a computer program or a device for performing the method of the invention and a computer device for executing this computer program.

The invention presented here:
- reveals information, which is not available currently for standard ECGs: the time course of the location of the cardiac electrical activity within a complete heartbeat (atrial activity, ventricular depolarization and repolarization).
- separates dipole location information from dipole momentum information, which is mixed up in standard ECG analysis.
- is capable to deduce the influence of body shape, tissue inhomogeneity and electrode position from the ECG measurements. This may allow more precise application of other ECG analysis methods (e.g. T-wave alternans, QRS-T angle, P-wave and T-wave dispersion).
- offers a new approach to identify slowly moving baseline wandering (even during AF, tachycardia, ectopic events).
- describes the cardiac electrical activity in terms of a physiological relevant 3-dimensional model.
- can use existing ECG measuring devices.
- can be applied to long term observations (Holter ECG).
- can be applied to any lead system with more than 3 leads.

DESCRIPTION OF FIGURES

FIG. 1 is an embodiment of the present invention for identification of the electrical activity in the heart concurrently with subject and measurement related conditions.

FIG. 2 shows the electrode positions of a standard resting ECG.

FIG. 3 shows the coordinate system, used for the description of spatial properties.

FIG. 4 is an excerpt of a 12-lead resting ECG with manually eliminated baseline wander, used for model adaptation in example 1.

FIG. 5 shows the prior electrode positions on the body surface, derived from the Dower matrix (FIG. 5(a)) and the estimated effective electrode positions together with the estimated time course of the moving dipole of one heartbeat (FIG. 5(b)), described in example 1.

FIG. 6 shows the estimated time course of the three spatial components of the dipole location (FIG. 6(a)) and dipole momentum (FIG. 6(b)) from example 1.

FIG. 7 compares the residuals of the full model of example 1 (FIG. 7(d)) with the measured signal (FIG. 7(a)) and the residuals, which will be obtained using a simplified model without adaptation of the subject and measurement related conditions (FIG. 7(b): non-moving dipole model, FIG. 7(c): moving dipole model).

FIG. 8 illustrates the capability of this invention to identify the signal baseline as described in example 2. FIG. 8(a) shows three measured leads of an ECG with atrial fibrillation and considerable baseline wander. FIG. 8(b) is the predicted lead voltage for the three leads, having the baseline removed.

FIG. 9 shows for one heartbeat the overlaid ECG signal (FIG. 9(a)) and the 3-dimensional time course of the dipole location with its associated momentum vector (FIG. 9(b)). Typical waveform patterns are indicated by arrows.

DETAILED DESCRIPTION

Definitions

In general, all terms used in this description have the meaning a skilled person will commonly understand.

As used in this description, a lead denotes an electrode configuration for measuring electric potentials, like the well-known Einthoven limb leads. In a lead two or more electrodes are combined and the difference of the electric potentials measured at one lead provides a lead voltage. In general, measurements and determinations or calculations performed in the methods of the invention are performed per a given time point and per a given lead.

As used in this description, a body surface potential is the electric potential at a body surface, generated by the electrical activity of the heart, which may be superimposed by other non-cardiac electrical sources like muscular activity or external electrical noise.

As used in this description, a baseline refers to the low frequency part of the electrical potential at a lead, disregarding the electrical activity of the heart and any high frequency noise. Ideally the baseline is just zero, but in reality lead measurements often show some offset changing with time, the so-called baseline wander.

As used in this description, the dipole momentum is a 3-dimensional vector that denotes the orientation and strength of a dipole. In the sense of the invention, the electrical activity of a heart is considered to form a single dipole.

As used in this description, a moving dipole considers the center of the electrical activity of the heart as moving around within the heart throughout the time course of a single heartbeat. If the center of the electrical activity of the heart is not considered to move considerably throughout the time course of a single heartbeat the dipole is called a non-moving dipole. However the location of a non-moving dipole in the sense of this description may change within the whole body due to a dislocation of the heart caused by body movement or respiration.

As used in this description, a tissue conductivity denotes the electrical conductivity of the tissues, lying between an electrical source within a body and a point at the body surface.

As used in this description, a decay exponent describes the decrease of a potential with increasing distance from a dipole source.

As used in this description, a conductivity parameter is a general term for a parameter which characterizes properties of the electrical conductivity in a body. In the sense of the invention, the tissue conductivity and the decay exponent are conductivity parameters.

As used in this description, a lead vector is a 3-dimensional transfer coefficient which describes how a dipole source at a certain point inside a volume conductor influences the potential at another field point within or on the surface of the volume conductor. The value of the lead vector depends on the location of the dipole, the location of the field point, the shape of the volume conductor and the distribution of the conductivity of the volume conductor (see [5], section 11.4).

As used in this description, a lead voltage may be measured via body surface potentials (measured lead voltage) and determined via a function depending from the dipole momentum vector, the lead vector and possibly a baseline value (determined lead voltage). In a preferred embodiment, the lead voltage is determined for each time point and each lead by calculating a scalar product of a dipole momentum vector with a lead vector plus, optionally, a baseline value. The lead vector to be multiplied with the momentum vector is the lead vector for the momentum vector at the same time point and at the same lead. Such a lead vector may be called the appropriated lead vector with respect to the momentum vector.

As used in this description, a sampling rate relates to the number of samples that are collected per time unit.

As used in this description, parameter is a general term for all properties that define the model which describes the electrical activity of the heart and which link it to the potential at the body surface. The parameter used in this description may be 1-dimensional or 3-dimensional. A 3-dimensional parameter typically denotes a spatial property where its spatial coordinates are referred to as x, y and z. Some of those parameters may be fixed, others are variable and their values are adjusted through a method of the invention. Parameters in the sense of the invention are the dipole momentum, denoted as q, the dipole location, denoted as p, the position of the electrodes, denoted as e, the tissue conductivity, denoted as $\sigma$, the decay exponent, denoted as $\kappa$ and the baseline at each lead, denoted as b.

As used in this description, a time course of a parameter relates to the description of a parameter whose values my change with time (like, the dipole momentum, the dipole location, electrode positions, etc.). For describing a time course of a parameter in the sense of the invention an interpolating function may be used, in particular a cubic spline. Such an interpolating function may be determined by a number of given support time points together with their associated parameter values. Parameter values for arbitrary time points in-between the support time points may be calculated by interpolation. Depending on the degree of variation of a parameter with time, the support time points may be arranged sparsely or densely. In this invention, a typical parameter with dense support may be the dipole momentum. It may be supported at each sampling time point or at any multiple of the sampling interval (e.g. at each 4th sampling point). A typical parameter with sparse support may be a baseline or an electrode position, which may be considered varying slowly according to the breathing cycle of the subject, having one support time point at every heartbeat. In case of a moving dipole the dipole location may be represented as a time course with dense support, similarly to the time course of the dipole momentum. In case of a non-moving dipole the dipole location may be represented as a time course with sparse support. Thus, a complete time course of a parameter is defined by a number of values $N_V$, which is given by $N_V$=number of support time points*parameter dimension.

As used in this description, values of a time course are in the case of the time course of a dipole location a set of values consisting of spatial coordinates denoting the location of said dipole, wherein for each time point a set of said values is provided.

As used in this description, values of a time course are in the case of the time course of a dipole momentum a set of values consisting of directional coordinates denoting the direction and strength of said dipole momentum, wherein for each time point a set of said values is provided.

As used in this description, an initial value or an initial value of a parameter as defined above relates to start values which are provided for a variable parameter wherein this parameter is to be varied during a method of the invention.

As used in this description, a condition characterizes those parameters which control the mapping of the electrical source onto the body surface potential. Some of those conditions are subject related (e.g. body geometry, tissue conductivity, decay exponent), others are measurement related (e.g. electrode position, baseline).

As used in this description, a prior condition relates to values arbitrarily chosen or derived from prior knowledge about a condition. Such prior knowledge may be derived from measurements, population statistics, or physical or mathematical models of the animal body. Prior conditions are a special set of initial values defined above which are used for subject and measurement related conditions. They are kept constant throughout the optimization process and deviation of the variable parameters from their prior values may be assessed within the regularizer functions (see below).

As used in this description, estimation, estimating, or estimate relates to the adaptation of variable parameters after performing an optimization process.

As used in this description, prediction, predicting, or predict relates to the determination of lead values by calculation based on the method of the invention.

As used in this description, a regularizer function $\Theta(x)$ is a positive valued function that measures the conformance of a parameter property with an expectation about that parameter property. Such property may be the value of the parameter, or any other property, like the curvature of a time course of the parameter. Good conformance will result in lower function values, less conformance will result in larger function values. A typical regularizer function e.g. may measure the deviation of the estimated parameter value x from its prior value $\tilde{x}$ through the function $\Theta(x, \tilde{x}) = \rho^2 \|x - \tilde{x}\|^2$ where $\rho$ determines how deviation from the expectation should be weighted. Another regularizer function may measure the curvature of the time course of a parameter, favouring smooth courses. Including regularizer functions into a minimization algorithm will prevent parameters from taking unexpected values. The choice of a specific regularizer function together with the choice of a specific regularizer weight is considered to be a regularizer setting. Thus a regularizer setting represents a subjective opinion about the expectation of a parameter property and how strong that parameter property may deviate from its expectation during an optimization process. Examples of regularizer functions are provided in the description, although the invention should not be understood to be limited to the regularizer functions disclosed in the description. In a preferred embodiment, a regularizer setting is provided for a method of the invention, i.e. a regularizer function with a regularizer weight is provided replacing a regularizer function.

As used in this description, an error function relates to a real-valued function that measures the goodness of fit of predicted values versus measured values and the deviation of adapted conditions versus their prior conditions. In a preferred embodiment of the invention, an error function considers the deviation of the measured lead voltages to the determined lead voltages and the results of the regularizer functions. In a particularly preferred embodiment, an error function is calculated as the sum of the deviation of the measured lead voltages to the determined lead voltages and the results of the regularizer functions.

As used in this description, an optimization algorithm relates to an optimization of a function, wherein a real function is minimized or maximized by systematically choosing or varying the values of real or integer variables from within an allowed set. In a preferred embodiment of the invention a non-linear optimization algorithm is applied.

As used in this description, non-linear optimization algorithm relates to an optimization of a function, wherein the function or the constraints or both contain nonlinear parts.

Non-linear optimization algorithms are generally known in the art. Preferred non-linear optimization algorithms may be conjugate gradient methods as described in [7].

As used in this description, degrees of freedom are the number of measurement values minus the number of adjustable parameter values used in an optimization process.

General Approach

This invention is based on a model, which describes the electrical activity of the heart in terms of a single moving dipole, where the dipole location p(t) describes the center of the electrical activity and the dipole momentum vector q(t) its direction and strength.

The electrical activity of the heart is detected at the body surface by a couple of electrodes at a larger number of sampling times. A detected potential at an electrode must be referred to another electrode in order to determine a potential difference, which is called a lead measurement. Given $N_E$ electrodes, $N_E-1$ independent leads can be derived. To each lead, a lead vector can be assigned in such a way that the observed lead measurement may be considered as projection of the dipole momentum vector with the appropriate lead vector. Mathematically this projection can be described as scalar product of the dipole momentum vector with the lead vector. The lead vector for a given pair of electrodes depends on the electrode positions, the location of the dipole and on subject related properties of the volume conductor (i.e. body geometry, tissue inhomogeneity and tissue conductivities).

The core novelty of this invention is a method which allows to estimate those time varying lead vectors concurrently with the time course of the moving dipole. This requires a mathematical model which describes the dependency of the lead vectors from the conditions mentioned above.

For an infinite, homogeneous volume conductor with conductivity σ the potential Φ of a dipole diminishes with distance r from its location p(t) as $\Phi(r) \cong 1/\sigma r^2$ ([5], section 8.2.2). For an electrode E at position ẽ having a remote reference, the direction of its associated lead vector is ẽ−p(t). The lead vector itself may be chosen as:

$$l_E(t) = \frac{\tilde{e} - p(t)}{\sigma \|\tilde{e} - p(t)\|^3} \quad (1)$$

For a real thorax, which must be considered as an inhomogeneous and finite volume conductor, formula (1) may be adjusted according following thoughts:
1. The conductivity σ may depend on the direction of the electrode E seen from the heart. Thus σ may be replaced in formula (1) by $\sigma_E$.
2. The decrease of the potential with distance from the dipole source in direction to electrode E, which in case of a homogeneous infinite volume conductor is characterized by the decay exponent κ=2, may be generalized as $\Phi_E(r) \cong 1/\sigma_E r^{\kappa_E}$.
3. Different organs with different conductivities will cause a deviation of the lead vector field. Thus a unipolar lead vector may not point directly from the dipole source to the electrode position, but rather represents its lead field direction in the neighborhood of the heart. This effective electrode position may be denoted as e.

Thus formula (1) may be adjusted as:

$$l_E(t) = \frac{e - p(t)}{\sigma_E \|e - p(t)\|^{1+\kappa_E}} \quad (2)$$

For a lead λ, whose measurement is determined by a weighted combination of the electric potentials of a set of electrodes $E_\lambda$, its lead vector $l_\lambda$ is (according to the linear relationship of lead vectors) the weighted sum of the appropriate electrode related lead vectors:

$$l_\lambda = \sum_{j \in E_\lambda} c_j \frac{e_j - p(t)}{\sigma_j \|e_j - p(t)\|^{1+\kappa_j}} \quad (3)$$

This adjustment may be considered as a parameterization of the lead vector field constituted by a given lead ([5], section 11.6).

In real world situations, body surface electrodes will also be affected by other electrical sources than from the heart. Such electrical noise may be characterized by any frequency band. Low frequency noise at a certain lead λ may be modelized as slowly varying baseline wander $b_\lambda(t)$. Putting everything together, the lead voltage $v_\lambda(t_i)$ at sampling time $t_i$ may be predicted as:

$$v_\lambda(t_i) = l_\lambda(t_i) \cdot q(t_i) + b_\lambda(t_i) \quad (4)$$

The electrode related parameters e, σ and κ are redundant in some way: If the dipole would not move at all, σ and κ could be encoded through the length of e. Furthermore the electrode positions may be rotated or scaled in the three dimensional space without substantial impact for the dipole estimate: Its location and momentum would also just be rotated and scaled appropriately. Such an arbitrary rotation and scaling can be prevented by using some prior knowledge about the real electrode positions and regularizing the deviation of the estimated electrode position e from the prior knowledge ẽ.

If all the electrode related parameters are given, at least six lead measurements are required to estimate the six unknown dipole components for a given time instance (i.e. 3 spatial components of the dipole location and 3 components of the dipole momentum vector). Therefore more than six lead measurements are needed and measurements have to be repeated at multiple time instances in order to gain enough degrees of freedom for further estimation of the electrode related conditions and the baseline. A minimum configuration could be a standard 12-lead resting ECG (having 8 quasi independent leads), sampled at 500 Hz and measured for at least one second.

The number of parameters to adapt may be reduced by modeling the dipole momentum and location as (cubic) splines with reduced number of support points (e.g. spline support at every 4th sampling point). Applying regularizers onto the time course of the dipole parameters may further increase the effective number of degrees of freedom. Such re-sampling and regularization of the dipole parameters has the effect of low-pass filtering onto the time course of those parameters.

In a real measurement situation (e.g. 24-hour Holter ECG), all parameters reflecting subject and measurement related conditions (e, σ, κ, b(t)), may change due to respiration, change of body position, activity or changing electrolyte conditions. These parameters may also be encoded as (cubic) spline with sparse support (e.g. spline support at every heartbeat).

The mathematical model which relates the equivalent moving dipole generator from the heart to the lead measurements is given through formula (4). Its parameters may be estimated by minimizing following error function F:

$$F = \sum_{i=1}^{N_S} \sum_{\lambda=1}^{N_\Lambda} w_{i,\lambda}^2 (m_\lambda(t_i) - v_\lambda(t_i))^2 + \Theta(q, p, \tilde{p}, b, \tilde{b}, e, \tilde{e}, \sigma, \tilde{\sigma}, \kappa, \tilde{\kappa}) \quad (5)$$

where $N_S$ is the number of samples, $M_\Lambda$ is the number of leads, $m_\lambda(t_i)$ the measurement, $v_\lambda(t_i)$ the voltage prediction at lead $\lambda$ at time instance $t_i$, $w_{i,\lambda}$ are some weights and $\Theta$ denotes some positive valued regularizer function, related to the individual parameter x and its prior value $\tilde{x}$. The weights $w_{i,\lambda}$ are considered given. They may be chosen as $w_{i,\lambda} \equiv 1$ or according to some other criteria (e.g. $w_{i,\lambda}^2 = 1/\mathrm{var}(\epsilon_{i,\lambda})$ where $\mathrm{var}(\epsilon_{i,\lambda})$ may denote the variance of the signal noise at lead $\lambda$ and time $t_i$). The error function F is non-linear. It may be minimized using any of the well-known algorithms for minimizing non-linear multidimensional functions.

The regularizer function $\Theta$ may be simplified as sum of regularizer components of the individual parameter elements $\Theta_q(q)$, $\Theta_p(p, \tilde{p})$, $\Theta_b(b, \tilde{b})$, $\Theta_e(e, \tilde{e})$, $\Theta_\sigma(\sigma, \tilde{\sigma})$, $\Theta_\kappa(\kappa, \tilde{\kappa})$. A regularizer component, applied to a spline implementation of a parameter, may use any derivation of the spline function for regularization. In this way the distance of the dipole location from the origin may be regularized by $$\Theta_{p_0}(p) = \rho_{p_0}^2 \sum_{i=1}^{N_S} \|p(t_i)\|.$$

The curvature $\ddot{q}(t)$ of the dipole momentum may be regularized by $$\Theta_{q_2}(q) = \rho_{q_2}^2 \sum_{i=1}^{N_S} \|\ddot{q}(t_i)\|^2.$$

Deviation of the $N_E$ estimated electrode positions e from their prior positions $\tilde{e}$ may be regularized by $$\Theta_e(e, \tilde{e}) = \rho_e^2 \sum_{j=1}^{N_E} \left\| \frac{e_j - \tilde{e}_j}{\|\tilde{e}_j\|} \right\|^2.$$

The electrode related tissue conductivities $\sigma$ should always be positive due to physical laws. This may be obtained by using $$\Theta_\sigma = \rho_\sigma^2 \sum_{j=1}^{N_E} (\log(\sigma_j) - \log(\tilde{\sigma}_j))^2.$$

The electrode specific decay exponent $\kappa$ may be considered as bounded with $\kappa \in (\kappa_l; \kappa_u)$ where $0 < \kappa_l < 2$ and $2 < \kappa_u$. The number 2 should be part of that interval because that value represents the homogeneous, infinite volume conductor. Let $\tau(\kappa)$ be a continuous, monotone mapping with $\tau: (\kappa_l; \kappa_u) \to (-\infty; \infty)$. The decay exponents may thus be regularized by $$\Theta_\kappa = \rho_\kappa^2 \sum_{j=1}^{N_E} \|\tau(\kappa) - \tau(\tilde{\kappa})\|^2.$$

If the geometry of the heart is given (e.g. by magnetic resonance imaging or computer tomography), estimation of the dipole location p(t) may be limited to the appropriate region. The choice of a certain regularizer function together with the choice of certain regularizer weights (e.g. $\rho_{p_0}$, $\rho_{q_2}$, $\rho_e$, $\rho_\sigma$ and $\rho_\kappa$ from the examples above) are named regularizer settings as given in FIG. 1.

The baselines may be determined by fitting a line or a spline to the individual lead measurements with support at a certain time point of each heartbeat (e.g. center of the PQ-interval or a time point, lying some milliseconds before the onset of the P-wave) and a baseline value, calculated on base of sample values from a certain region close to the support time point (e.g. mean or median value of the referenced sample values). Another approach to estimate the baselines may be to include the baseline parameters into the general model optimization procedure and to apply a special regularization approach: Consider a dipole source generator with zero momentum strength. Any baseline wandering at one or more leads will enforce the model fitting process to predict the observed lead measurements by estimating a non-zero dipole momentum. If a non-zero dipole strength is uniformly distributed in the 3-dimensional space, any baseline will increase the estimated value of the dipole strength integral. Thus minimizing the integral of the dipole strength $\|q(t)\|$ may yield useful estimates of the baseline. This can be done by using the regularizer component $$\Theta_{q_0} = \rho_{q_0}^2 \sum_{i=1}^{N_S} \|q(t_i)\|.$$

It is obvious that there may be some conditions where this approach will lead to a biased estimate: Consider a zero baseline with non-zero dipole momentum pointing to a certain electrode. The minimizing approach described above probably will underestimate the dipole strength at the expense of a non-zero baseline estimation. When the proposed regularizer component $\Theta_{q_0}$ is used, minimizing formula (5) will result in a biased estimate of the electrode positions, as a lower estimated distance of the electrodes to the dipole location will also decrease the term $\Theta_{q_0}$. It is therefore recommended to run the optimization process iteratively in multiple steps:

Step A may minimize (5) where $\Theta$ contains a regularizer component of type $\Theta_{q_0}$ without varying the electrode positions.

Step B may minimize (5) where $\Theta$ does not contain any regularizer component of type $\Theta_{q_0}$ and where electrode positions are free movable.

Each of these steps may be run any number of iterations. Sequence A-B may be repeated until some user defined convergence criterion is fulfilled.

FIG. 1 illustrates one preferred embodiment of the present invention. Electrocardiographic signals are recorded from a human subject 1 by a standard ECG recording system 2, delivering measured lead signals 3. Approximate electrode positions may be determined on base of the subjects size, chest circumference and gender, using the coordinate system shown in FIG. 3. These approximate electrode positions will be used as prior conditions 4, together with tissue conductivity $\sigma=1$ and decay exponent $\kappa=2$. The moving dipole model 5 may be initialized by setting its location p(t) to the origin of the coordinate system. The time course of its dipole momentum q(t) may be initialized by applying the method given in [9], using the lead vectors derived from the prior conditions 4 with help of formula (3). The optimization process 7 may be started and repeated for a certain number of iterations, comparing the measured ECG 3 with the predicted ECG 6, while applying some regularizer settings, defined in 8. Estimated model parameters may be inspected visually 9 and standard regression analysis methods (e.g. residual analyses) may be used to check the goodness of fit. The optimization process may be continued or restarted using modified regularizer settings until the user accepts the identified model.

This invention also covers the especial case of a non-moving dipole. Estimation of the three spatial components of the dipole momentum vector requires just three lead measurements per time instance, compared to the six leads for the moving dipole. The decay exponent $\kappa$ mentioned above is not applicable in a non-moving dipole approach as it describes the dependency of the potential from the distance to the electrical source—which is considered constant in that especial model.

Embodiments of the Invention

This invention relates to a method for identifying the electrical activity in the heart of an animal body in terms of a single dipole, which may be considered moving or non-moving, from measurements from body surface potentials, concurrently estimating subject and measurement related conditions, comprising the steps of:

1. measuring body surface potentials of an animal body by multiple leads via electrodes positioned on the animal body, thereby producing measurements of lead voltages at a given number of time points;
2. providing prior values for a time course of the dipole location, of the electrode positions on the body, of the tissue conductivity and of the decay exponent with respect to each electrode, as well as prior values for the time course of the baseline at each lead, herein after referred to as prior conditions;
3. providing initial values for a time course of the dipole momentum and initial values for all parameters of step 2;
4. providing regularizer functions for the dipole momentum, dipole location, electrode positions, tissue conductivities, decay exponents and baselines;
5. determining a lead voltage for each lead and each time point by calculating a scalar product of a dipole momentum vector with a lead vector plus a baseline value, wherein the lead vectors are determined by the dipole location, the positions of the electrodes, the tissue conductivities and the decay exponents;
6. calculating an error function which considers deviation of the measured lead voltages of step 1 to the lead voltages determined in step 1e and the results of the regularizer functions of step 4;
7. minimizing the error function of step 1f by applying an optimization algorithm, varying the dipole momentum and optionally any values of step 3;
8. repeating steps 5 to 7 until an optimization criterion is met;
9. outputting the time courses of the dipole momentum, dipole location, electrode positions, tissue conductivities, decay exponents and baselines.

The animal of the invention may be a mammal. In a particular preferred embodiment the mammal may be a human. However, the invention can also be applied to any domestic animal or pet.

In a preferred embodiment of the invention, the number of leads should be at least 4 in case of a non-moving dipole and it should be at least 7 in case of a moving dipole. Number of electrodes may be 10 as in the case of standard 12-lead measurements or it may be up to several hundreds as used for body surface potential measurements. In general, the electrodes can be positioned on the body at any position the person skilled in the art of electrocardiography would use for preparing a standard electrocardiogram or a body surface potential map, but the use of non standard positions is also within the scope of the invention.

Generally any number of electrodes could be combined to form a lead. In a preferred embodiment, the number of electrodes to be combined is 2 as in case of the well-known limb leads. In another embodiment, the number of electrodes to be combined is 4 as in the case of the well-known precordial leads.

Measuring the body surface potentials may be performed for any length of time, preferentially between 10 seconds and one minute. Measurement may be taken continuously (e.g. 10-second resting ECG) or intermittently (e.g. multiple sections from a 24-hour Holter ECG). The potential may be measured at a certain sampling rate, preferentially between 100 Hz and 1000 Hz.

In a preferred embodiment of the invention, the time courses of parameters are described by interpolating functions, in particular, by cubic spline functions. The density of the support time points for the interpolating functions may be chosen according to the degree of variation of the parameter with time. For the dipole momentum and position, support time points may be chosen at every sampling time point or at some multiple of the sampling interval (e.g. every 2nd, 4th, 8th sampling time point). For the electrode positions, the tissue conductivities, the decay exponents and the baselines, support time points may be chosen at every heartbeat.

In an alternative embodiment of the invention, the dipole is considered a non-moving dipole.

In another alternative embodiment of the invention, the electrode positions, the tissue conductivities or the decay exponents are considered not to change with time.

In a preferred embodiment, the regularizer functions encode prior knowledge about the mentioned parameters and consider deviation of the values of step 3 to their prior values of step 2.

In a preferred embodiment, the values of step 3 to be varied are selected from the group consisting of the values for a time course of the dipole location, of the electrode positions on the body, of the tissue conductivity and of the decay exponent with respect to each electrode, as well as the values for the time course of the baseline at each lead.

In a preferred embodiment, the values of step 3 to be varied are the values for a time course of the dipole location, of the electrode positions on the body, of the tissue conductivity and of the decay exponent with respect to each electrode, as well as the values for the time course of the baseline at each lead or any subset of these values.

In a preferred embodiment of the invention, the prior conditions are derived from body measurements, population statistics, or physical or mathematical models of the animal body. The regularizer function may be a sum of regularizer functions for the individual parameters. The regularizer functions of the invention may be provided by choosing regularizer settings for regularizing deviation of estimated conditions from their prior values of said conditions and/or choosing regularizer functions for the time courses of those parameters which are varying with time. A regularizer function may regularize the distance of the estimated dipole location from its prior value, which may be chosen arbitrarily. If the geometry of the heart is given, the estimate of the dipole location may be limited to a region within the heart wherein the region is defined by the geometry of the heart. The origin of the coordinate system may be chosen to be any position in the heart, preferentially in the center of the heart's mass. A regularizer function may regularize the curvature of the dipole moment and/or the curvature of the dipole location.

In a further embodiment of the invention, the tissue conductivity and/or decay exponent depends on the direction of the electrode from the heart. Thus, each electrode may be associated with a different tissue conductivity and/or decay exponent.

In a further embodiment of the invention the electrode positions may slowly vary with time, thus modeling breathing conditions.

In a further embodiment of the invention the optimization is performed by minimizing the following function:

$$F = \sum_{i=1}^{N_S} \sum_{\lambda=1}^{N_A} w_{i,\lambda}^2 (m_\lambda(t_i) - v_\lambda(t_i))^2 + \Theta(q, p, \tilde{p}, b, \tilde{b}, e, \tilde{e}, \sigma, \tilde{\sigma}, \kappa, \tilde{\kappa})$$

where $N_S$ is the number of samples, $N_A$ is the number of leads, $m_\lambda(t_i)$ the measurement at lead $\lambda$ at time instance $t_i$, $v_\lambda(t_i)$ the voltage prediction at lead $\lambda$ at time instance $t_i$, $w_{i,\lambda}$ are chosen weights and $\Theta$ denotes a positive valued regularizer function, and wherein $q=q(t)$ is the dipole momentum vector, $p=p(t)$ is the location of the dipole, $\tilde{p}$ are prior values of p, $b=b(t)$ is a collection of the baseline at all leads, $\tilde{b}$ are prior values of b, $e=e(t)$ is a collection of the estimated positions of all electrodes, $\tilde{e}$ are prior values of e, $\sigma=\sigma(t)$ is a collection of the conductivities of the tissue between the heart and the electrodes, $\tilde{\sigma}$ are prior values of $\sigma$, $\kappa=\kappa(t)$ is a collection of the decay exponents, characterizing the decay of the electrical potential in direction to an electrode, $\tilde{\kappa}$ are prior values of $\kappa$.

Weights and regularizer functions are generally known in the art and the skilled person is in the position to determine appropriate weights and regularizer functions based on the information provided in this description.

In a further embodiment of the invention the voltage prediction is $$v_\lambda(t_i) = l_\lambda(t_i) \cdot q(t_i) + b_\lambda(t_i),$$

wherein $l_\lambda(t_i)$ is the lead vector at lead $\lambda$ at time instance $t_i$, $q(t_i)$ is the dipole momentum vector at time instance $t_i$ and $b_\lambda(t_i)$ is the baseline at lead $\lambda$ and time instance $t_i$.

In a further embodiment of the invention the lead vector is $$l_\lambda(t_i) = \sum_{j \in E_\lambda} c_j \frac{e_j(t_i) - p(t_i)}{\sigma_j(t_i) \|e_j(t_i) - p(t_i)\|^{1+\kappa_j(t_i)}}$$

wherein $E_\lambda$ is the set of all electrodes onto which lead $\lambda$ is based, $c_j$ is the combination weight of the electrode j for determination of lead $\lambda$, $e_j(t_i)$ is the position vector of electrode j at time instance $t_i$, $p(t_i)$ is the dipole location vector at time instance $t_i$, $\sigma_j(t_i)$ is the estimated conductivity of the tissue between the heart and the electrode j at time instance $t_i$ and $\kappa_j(t_i)$ is the decay exponent for electrode j at time instance $t_i$.

In a further embodiment of the invention, any of the conditions mentioned in step 3 may be kept constant during the optimization process in step 7.

In a further embodiment of the invention the location and momentum of said dipole are visualized for each time point. Visualization can be performed with any suitable means, in particular, with a display, computer screen, print out, plot out. The skilled person is aware of further and additional means for visualizing the location and momentum of a dipole. The location and momentum of said dipole can be denoted in the same or different visualizations in black and white or in color and each of said features of the dipole may be visualized in different colors or shades of gray.

A preferred embodiment of the invention relates to a computer program for performing the method of the preceding claims, wherein loading of said computer program into a computer causes the computer to perform the method of the preceding claims. In a further embodiment of the invention a data carrier contains said computer program of the invention. Any available data carrier know in the art is envisioned, like memory stick, hard disk, floppy disk, zip disk, CD-ROM, DVD-ROM or any other data carrier that can store information, e.g. in an optical and/or magnetic form.

A further embodiment of the invention relates a computer device containing said data carrier of the invention and is, optionally, executing said program. Any computer device that performs the necessary calculations in reasonable time, e.g. hours or days is suitable. The computer devices may also be combined with any other non computer device.

A yet further embodiment of the invention relates to a device or means for performing the method of the preceding claims. This includes also devices which are capable of performing the methods of the invention in a not computer device based way. The method of the invention may be combined with other methods, like computer or non computer based methods. These methods can also be diagnostic or therapeutic methods, in particular methods, for the diagnosis and therapy of heart diseases.

EXAMPLE 1

Standard 12-Lead Resting ECG

A typical realization of the invention may use the measurements of lead I, II, V1, V2, V3, V4, V5 and V6 of a standard 12-lead resting ECG, which may be sampled with 500 Hz for a time length of 10 seconds, resulting in 5000 samples per lead or 40000 potential measurements. The baselines at the eight leads may be removed in advance by subtracting a spline function from the signal, which may be attached 10 milliseconds before the P-wave onset (see FIG. 4).

Prior knowledge about the electrode positions may be derived using the Dower matrix [2]. Each row of that matrix can be interpreted as lead vector of the eight leads mentioned above, with a non-moving heart dipole located at the origin of the coordinate system (FIG. 3). Assuming that the electrode at the right arm is located at x=0, y=−2 and z=0.5, the positions of the other eight electrodes can be chosen in such a way, that the resulting lead vectors harmonize with the Dower matrix (see FIG. 5(a)). For each electrode the prior value for the associated tissue conductivity and decay exponent may be chosen as $\sigma=1$ and $\kappa=2$. Electrode positions, tissue conductivities and decay exponents may not change with time.

Location and momentum of the dipole may be interpolated by a cubic spline, where every 4th sampling time point may be used as spline support time point. This will create 1250 support time points, each carrying 6 parameters (i.e. 3-dimensional dipole location and momentum), resulting in 7500 adjustable parameters. The positions of the nine used electrodes have to be estimated by 27 adjustable parameters. Estimation of the electrode related conductivities and decay exponents will add another 18 adjustable parameters. All in all there will be 7545 adjustable parameters, given 40000 measurements.

The optimization process may be regularized by using the regularizer function $\Theta=\Theta_e+\Theta_\sigma+\Theta_\kappa$ as mentioned above with regularizer weights $\rho_e=4$, $\rho_\sigma=4$ and $\rho_\kappa=4$. The curvature of the time course of the dipole location and momentum may not be regularized in this example. The weights $w_{i,j}$ in formula 5 may be chosen constant as $w_{i,j}=1$. Using a conjugate gradient method for minimizing the error function and applying 400 iterations, the optimization process takes about one hour calculation time on a one-processor 3 GHz computer.

The estimated effective electrode positions are shown in FIG. 5($b$). This figure furthermore shows the time course of the dipole location of one single heartbeat, with the dipole momentum vectors attached to the location line. FIG. 6 shows the 3-dimensional time course of the dipole location and momentum for a couple of heartbeats. It may be noted that the estimated dipole location does not only cover the movement of the electrical activity in the heart itself, but also reflects the physical movement of the heart caused by respiration and heartbeat contraction.

Inspection of the residuals $m(t_i)-v(t_i)$ will yield information about the quality of the model adaptation. FIG. 7 compares the residual of the given example with approaches, omitting adaptation of the measurement and subject related conditions: FIG. 7($a$) shows a magnified overlay of the ECG signal from FIG. 4. FIG. 7($b$) shows the residuals resulting from a non-moving dipole model and FIG. 7($c$) shows the residuals resulting from a moving dipole model, both using the prior conditions. FIG. 7($d$) shows the residuals resulting from the model described above. It reveals evidence that the presented approach is capable in describing the majority of the ECG signal information.

EXAMPLE 2

Baseline Estimation in an ECG showing Atrial Fibrillation

Atrial or ventricular arrhythmia often generate ECGs without electrically silent parts, which indicate the signal baseline. This example shows how the optimization process may be customized, in order to estimate the baselines concurrently with the estimate of the moving dipole and the adaptation of the measurement and subject related conditions.

A typical realization will use the same leads, sampling time and prior conditions as in example 1. The baselines to estimate may be described as cubic spline, attached some milliseconds before depolarization onset of each heartbeat. The baseline amplitudes may be initialized with zero values. The two optimization steps may be configured as follows:

Step A may use the regularizer component $\Theta_{q_0}$ mentioned above with $\rho_{q_0}=1$, varying the dipole location p(t), momentum q(t) and the baseline b(t), while keeping all other parameter constant.

Step B may use the regularizer components $\Theta_e$, $\Theta_\sigma$ and $\Theta_\kappa$ mentioned above with $\rho_e=\rho_\sigma=\rho_\kappa=4$, varying the dipole location p(t), momentum q(t), electrode positions e, tissue conductivities $\sigma$ and decay exponent $\kappa$, while keeping the baseline constant.

Each step may run 100 iterations to minimize the appropriate error function. The step sequence A-B may be repeated four times, followed by a final step B with another 300 iterations.

FIG. 8 shows an excerpt of an ECG, indicating atrial fibrillation. The lead measurements show considerable baseline wander (FIG. 8($a$)). The predicted lead voltages however are well centered and very similar to the original measurements (8($b$)).

References

[1] Gordon E. Dower. Signal processing apparatus and method for adding additional chest leads to the 12-lead electrocardiogram without additional electrodes, 1998. U.S. Pat. No. 5,711,304.

[2] Lars Edenbrandt and Olle Pahlm. Vectorcardiogram synthesized from a 12-lead ECG: Superiority of the inverse dower matrix. *Journal of Electrocardiology*, 21:361-367, 1988.

[3] E. Frank. An accurate, clinically practical system for spatial vectorcardiography. *Circulation*, 13: (5) 737-749, 1956.

[4] Bin He. Method and apparatus for three dimension electrocardiographic imaging, 2005. U.S. Pat. No. 6,856,830 B2.

[5] Jaakko Malmivuo and Robert Plonsey. *Bioelectromagnetism—Principles and Applications of Bioelectric and Biomagnetic Fields*. Oxford University Press, 1995.

[6] Charles Olson. Three dimensional vector cardiographic display and method for displaying same, 1998. U.S. Pat. No. 5,803,084.

[7] William H. Press, Saul A. Teukolsky, William T. Vetterling, and Brian P. Flannery. *Numerical Recipes: The Art of Scientific Computing*. Cambridge University Press, 2007.

[8] Yoram Rudy. System and methods for noninvasive electrocardiographic imaging (ecgi) using generalized minimum residual (gmres), 2006. U.S. Pat. No. 7,016,719 B2.

[9] Pierre Savard, Fernand A. Roberge, Jean-Benot Perry, and Reginald A. Nadeau. Representation of cardiac electrical activity by a moving dipole for normal and ectopic beats in the intact dog. *Circulation Research*, 46:415-425, 1980.

The invention claimed is:

1. A method for identifying the electrical activity in a heart of a mammalian body in terms of a single dipole from measurements from body surface potentials, concurrently estimating subject and measurement related conditions, comprising the steps of:

a) measuring body surface potentials of a mammalian body by multiple leads via electrodes positioned on the mammalian body, thereby producing measurements of lead voltages at a given number of time points;

b) providing prior values for a time course of the dipole location and of parameters reflecting the subject and measurement related conditions, wherein said parameters are the electrode positions on the mammalian body, conductivity parameters including the tissue conductivity and the decay exponent with respect to each electrode, together with said prior values for the time course of the baseline at each lead, which are collectively used as prior conditions, wherein the prior conditions are kept constant throughout an optimization process;

c) providing initial values for a time course of the dipole momentum and initial values for all parameters of step 1b, said initial values being used as the starting values in the optimization process;

d) providing regularizer functions for the properties of dipole momentum, dipole location, electrode positions, tissue conductivities, decay exponents and baselines, wherein said regularizer functions measure the conformance of said properties with an expectation about said properties, wherein said regularizer functions are based on said prior conditions;

e) determining a lead voltage for each lead and each time point by calculating a scalar product of the estimated dipole momentum vector with a lead vector plus an estimated baseline value, wherein the lead vectors are determined by estimates of the dipole location, the positions of the electrodes, the tissue conductivities and the decay exponents;

f) formulating an error function calculated using a deviation of the measured lead voltages of step 1a to the lead voltages determined in step 1e and the measurements calculated according to the regularizer functions of step 1d;

g) minimizing the error function of step 1f by applying an optimization algorithm, varying the dipole momentum and optionally any values of step 1c, thereby optimizing the estimated values of said parameters of step 1b;

h) repeating steps 1e to 1g until an optimization criterion is met; and i) outputting the time courses of the dipole momentum, dipole location, electrode positions, tissue conductivities, decay exponents and baselines.

2. The method of claim 1, wherein any of the conditions of step 1b are considered not to change with time.

3. The method according to claim 1, wherein the error function is:

$$F = \sum_{i=1}^{N_S} \sum_{\lambda=1}^{N_\Lambda} w_{i,\lambda}^2 (m_\lambda(t_i) - v_\lambda(t_i))^2 + \Theta(q, p, \tilde{p}, b, \tilde{b}, e, \tilde{e}, \sigma, \tilde{\sigma}, \kappa, \tilde{\kappa})$$

and wherein $N_S$ is the number of samples, $N_\Lambda$ is the number of leads, $m_\lambda(t_i)$ is the measurement at lead $\lambda$ at time instance $t_i$, $v_\lambda(t_i)$ is the lead voltage determined in step 1e at lead $\lambda$ at time instance $t_i$, $w_{i,\lambda}$ are chosen weights and $\theta$ denotes a positive valued regularizer function, and wherein $q=q(t)$ is the dipole momentum vector, $p=p(t)$ is the location of the dipole, $\tilde{p}$ are prior values of p, $b=b(t)$ is a collection of the baseline at all leads, $\tilde{b}$ are prior values of b, $e=e(t)$ is a collection of the estimated positions of all electrodes, $\tilde{e}$ are prior values of e, $\sigma=\sigma(t)$ is a collection of the conductivities of the tissue between the heart and the electrodes, $\tilde{\sigma}$ are prior values of $\sigma$, $\kappa=\kappa(t)$ is a collection of the decay exponents characterizing the decay of the electrical potential in direction to an electrode, and $\tilde{\kappa}$ is are prior values of $\kappa$.

4. The method according to claim 1, wherein the lead voltage determined in step 1e is $$v_\lambda(t_i) = l_\lambda(t_i) \cdot q(t_i) + b_\lambda(t_i)$$

and wherein $l_\lambda(t_i)$ is the lead vector at lead $\lambda$ at time instance $t_i$, $q(t_i)$ is the dipole momentum vector at time instance $t_i$, and $b_\lambda(t_i)$ is the baseline at lead $\lambda$ and time instance $t_i$.

5. The method according to claim 1, wherein the lead vector is $$l_\lambda(t_i) = \sum_{j \in E_\lambda} c_j \frac{e_j(t_i) - p(t_i)}{\sigma_j(t_i) \|e_j(t_i) - p(t_i)\|^{1+\kappa_j(t_i)}}$$

and wherein $E_\lambda$ is the set of all electrodes onto which lead $\lambda$ is based, $c_j$ is the combination weight of the electrode j for determination of lead $\lambda$, $e_j(t_i)$ is the position vector of electrode j at time instance $t_i$, $p(t_i)$ is the dipole location vector at time instance $t_i$, $\sigma_j(t_i)$ is the conductivity of the tissue between the heart and the electrode j at time instance $t_i$, and $k_j(t_i)$ is the decay exponent for electrode j at time instance $t_i$.

6. The method according to claim 5, wherein the decay exponent is 2.

7. The method according to claim 1, wherein prior conditions of step 1b are derived from body measurements, population statistics, or physical or mathematical models of a mammalian body.

8. The method according to claim 1, wherein the time course of the electrode positions, tissue conductivities, decay exponents, dipole momentum vector, dipole location and baselines are interpolated with mathematical functions capable of interpolating a cubic spline.

9. The method according to claim 1, wherein the optimization algorithm is a non-linear optimization algorithm.

10. The method according to claim 9, wherein the non-linear optimization algorithm is a conjugate gradient method.

11. The method according to claim 1, wherein said method is combined with a second method and performed on a computing device or a non-computing device.

12. The method according to claim 11, wherein said second method is a diagnostic or therapeutic method.

13. The method according to claim 12, wherein said diagnostic or therapeutic method is for the diagnosis or treatment of heart disease.

14. A non-transitory computer program product comprising a computer readable storage medium having computer program logic recorded thereon that when executed causes a computer processor to perform the method according to claim 1.

15. The computer program product according to claim 14, wherein the computer readable storage medium is a data carrier.

16. A computer device comprising a processor and a memory coupled to the processor, wherein the memory comprises the computer program product according to claim 14.

* * * * *